US011478567B2

(12) United States Patent
Seibel et al.

(10) Patent No.: US 11,478,567 B2
(45) Date of Patent: Oct. 25, 2022

(54) PHOTOSENSITIVE MEDICAL TAPE

(71) Applicant: University of Washington, Seattle, WA (US)

(72) Inventors: Eric J. Seibel, Seattle, WA (US); Leonard Nelson, Seattle, WA (US)

(73) Assignee: University of Washington, Seattle, WA (US)

( * ) Notice: Subject to any disclaimer, the term of this patent is extended or adjusted under 35 U.S.C. 154(b) by 855 days.

(21) Appl. No.: 15/778,935

(22) PCT Filed: Nov. 21, 2016

(86) PCT No.: PCT/US2016/063156
§ 371 (c)(1),
(2) Date: May 24, 2018

(87) PCT Pub. No.: WO2017/091515
PCT Pub. Date: Jun. 1, 2017

(65) Prior Publication Data
US 2018/0353640 A1      Dec. 13, 2018

Related U.S. Application Data

(60) Provisional application No. 62/259,535, filed on Nov. 24, 2015.

(51) Int. Cl.
*A61L 15/58*      (2006.01)
*A61L 15/42*      (2006.01)
(Continued)

(52) U.S. Cl.
CPC .............. *A61L 15/58* (2013.01); *A61F 13/02* (2013.01); *A61F 13/0226* (2013.01);
(Continued)

(58) Field of Classification Search
CPC .................................................. C09J 2203/37
See application file for complete search history.

(56) References Cited

U.S. PATENT DOCUMENTS 5,029,957 A      7/1991 Hood
5,156,911 A     10/1992 Stewart
(Continued)

FOREIGN PATENT DOCUMENTS

CN      203763360 U     8/2014
CN      209111633       7/2019
(Continued)

OTHER PUBLICATIONS

Laulicht et al., "Quick-release medical tape," PNAS, 2012, vol. 109, Issue 46, pp. 18803-18808.
(Continued)

*Primary Examiner* — Frank D Ducheneaux
(74) *Attorney, Agent, or Firm* — Christensen O'Connor Johnson Kindness PLLC (57) ABSTRACT

A photosensitive medical tape includes a backing layer that is at least partially transparent to a first spectrum of electromagnetic radiation. The photosensitive medical tape also includes a coupling layer disposed on a first side of the backing layer to provide adhesion of the photosensitive medical tape to the human skin. The photosensitive medical tape is disposed to absorb a second spectrum of electromagnetic radiation to decrease a strength of the adhesion provided by the coupling layer. The photosensitive medical tape is also flexible.

18 Claims, 8 Drawing Sheets

(51) Int. Cl.
*A61F 13/02* (2006.01)
*A61M 25/02* (2006.01)
*C09J 7/20* (2018.01)
*C09J 7/29* (2018.01)
*C08K 3/013* (2018.01)
*C08K 5/00* (2006.01)
*A61F 13/00* (2006.01)

(52) U.S. Cl.
CPC ............. *A61L 15/42* (2013.01); *A61M 25/02* (2013.01); *C08K 3/013* (2018.01); *C08K 5/0041* (2013.01); *C09J 7/20* (2018.01); *C09J 7/29* (2018.01); *A61F 2013/00182* (2013.01); *A61F 2013/00846* (2013.01); *C09J 2203/37* (2020.08); *C09J 2301/122* (2020.08); *C09J 2301/30* (2020.08); *C09J 2301/408* (2020.08); *C09J 2301/41* (2020.08)

(56) References Cited

U.S. PATENT DOCUMENTS

| | | | |
|---|---|---|---|
| 5,412,035 | A | 5/1995 | Schmitt et al. |
| 5,468,821 | A | 11/1995 | Lucast et al. |
| 6,066,156 | A | 5/2000 | Yan |
| 6,540,704 | B1 | 4/2003 | Bodenschatz et al. |
| 6,610,762 | B1 | 8/2003 | Webster |
| 7,465,142 | B2 | 12/2008 | Yoo |
| 7,896,053 | B2 | 3/2011 | Simandl et al. |
| 8,323,250 | B2 | 4/2012 | Chong et al. |
| 2004/0177918 | A1 | 9/2004 | Murata et al. |
| 2005/0037279 | A1 | 2/2005 | Miyako et al. |
| 2005/0277729 | A1 | 12/2005 | Tsunemine et al. |
| 2006/0110596 | A1 | 5/2006 | Palasz et al. |
| 2007/0010776 | A1 | 1/2007 | Price et al. |
| 2009/0081469 | A1 | 3/2009 | Oka et al. |
| 2009/0081849 | A1 | 3/2009 | Yamazaki et al. |
| 2010/0215947 | A1 | 8/2010 | Yamanaka et al. |
| 2010/0316845 | A1 | 12/2010 | Rule et al. |
| 2011/0224593 | A1 | 9/2011 | Tunius |
| 2012/0021215 | A1 | 1/2012 | Burch |
| 2012/0172949 | A1 | 7/2012 | Wagenaar Cacciola et al. |
| 2013/0017246 | A1 | 1/2013 | Tunius |
| 2013/0084459 | A1 | 4/2013 | Larson et al. |
| 2014/0018718 | A1 | 1/2014 | Rosing |
| 2015/0150731 | A1 | 6/2015 | Hatanaka et al. |

FOREIGN PATENT DOCUMENTS

| | | |
|---|---|---|
| EP | 2 957 610 A1 | 12/2015 |
| JP | 2015025932 | 2/2015 |
| JP | 2015059154 | 3/2015 |
| JP | 2016138182 | 8/2016 |
| JP | 2019203054 | 11/2019 |
| KR | 20200020114 | 2/2020 |
| TW | 453862 | 9/2001 |
| TW | 200418949 | 10/2004 |
| TW | 201945489 | 12/2019 |
| TW | 201946994 | 12/2019 |
| WO | 97/12561 A3 | 4/1997 |
| WO | 2013/184944 A1 | 12/2013 |

OTHER PUBLICATIONS

Bernatchez, "Care of Peripheral Venous Catheter Sites: Advantages of Transparent Film Dressings Over Tape and Gauze," Journal for the Association of Vascular Access, 2014, vol. 19, pp. 256-261.

Chivers, "Easy removal of pressure sensitive adhesives for skin applications," International Journal of Adhesion and Adhesives, 2001, vol. 21, pp. 381-388.

Lim et al., "Proof of Concept of a Surrogate High-Adhesion Medical Tape Using Photo-Thermal Release for Rabid and Less Painful Removal," Journal of Medical Devices vol. 14/021001, Jun. 1-11, 2020.

United States Food and Drug Administration Department of Health and Human Services, 2017, "Code of Federal Regulations Title 21, Section 880.5240: Medical Adhesive Tape and Adhesive Bandage," United States Food and Drug Administration Department of Health and Human Services, Silver Spring, MD, Standard No. 21CFR880.5240.

Van Schaik, R., and Rovekamp, M. H., 2011, "Fact or Myth? Pain Reduction in Solvent-Assisted Removal of Adhesive Tape," J. Wound Care, 20(8), pp. 380-383.

McNichol, L., Lund, C., Rosen, T., and Gray, M., 2013, "Medical Adhesives and Patient Safety: State of the Science: Consensus Statements for the Assessment, Prevention, and Treatment of Adhesive-Related Skin Injuries," J. Dermatol. Nurses. Assoc., 5(6), pp. 323-338.

Zhao, H., He, Y., Huang, H., Ling, Y., Zhou, X., Wei, Q., Lei, Y., and Ying, Y., 2018, "Prevalence of Medical Adhesive-Related Skin Injury at Peripherally Inserted Central Catheter Insertion Site in Oncology Patients," J. Vasc. Access, 19(1), pp. 23-27.

Ratliff, C. R., 2017, "Descriptive Study of the Frequency of Medical Adhesive-Related Skin Injuries in a Vascular Clinic," J. Vasc. Nurs., 35(2), pp. 86-89.

Ousey, K., Cooper, K., Fumarola, S., and Hitchcock, J., 2017, "Findings From a Multidisciplinary Focus Group Meeting to Discuss the Issue of Medical Adhesive-Related Skin Injury (MARSI) in the UK: The Way Forward," Wounds UK, 13(4), pp. 141-145.

Wang, D., Xu, H., Chen, S., Lou, X., Tan, J., and Xu, Y., 2019, "Medical Adhesive-Related Skin Injuries and Associated Risk Factors in a Pediatric Intensive Care Unit," Adv. Skin Wound Care, 32(4), pp. 176-182.

Farris, M. K., Petty, M., Hamilton, J., Walters, S.-A. A., and Flynn, M. A., 2015, "Medical Adhesive-Related Skin Injury Prevalence Among Adult Acute Care Patients," J. Wound, Ostomy Continence Nurses, 42(6), pp. 589-598.

Ullman, A. J., Kleidon, T., Gibson, V., McBride, C. A., Mihala, G., Cooke, M., and Rickard, C. M., 2017, "Innovative Dressing and Securement of Tunneled Central Venous Access Devices in Pediatrics: A Pilot Randomized Controlled Trial," BMC Cancer, 17(1), p. 595.

Taroc, A.-M., 2015, "Staying Out of Sticky Situations: How to Choose the Right Tape for Your Patient," Wound Care Advis., 4(6), pp. 21-26.

Manriquez, S., Loperfido, B., and Smith, G., 2014, "Evaluation of a New Silicone Adhesive Tape Among Clinicians Caring for Patients with Fragile or At-Risk Skin," Adv. Ski. Wound Care, 27(4), pp. 163-170.

De Crevoisier, G., Fabre, P., Corpart, J. M., and Leibler, L., 1999, "Switchable Tackiness and Wettability of a Liquid Crystalline Polymer," Science, 285(5431), pp. 1246-1249.

Kamperman, M., and Synytska, A., 2012, "Switchable Adhesion by Chemical Functionality and Topography," J. Mater. Chem., 22(37), pp. 19390-19401.

Boyne, J., Millan, E., and Webster, I., 2001, "Peeling Performance of a Novel Light Switchable Pressure-Sensitive Adhesive," Int. J. Adhes. Adhes., 21(1), pp. 49-53.

Clearweld, 2011, "Clearweld 900 Series Product Guide," Gentex Corporation, Carbondale, PA, accessed Nov. 6, 2019, http://www.clearweld.com/cms-assets/documents/Clearweld_900_Series_Coatings_Guide-web.pdf.

Klein, R., 2012, Laser Welding of Plastics: Materials, Processes and Industrial Applications, Wiley, Hoboken, NJ.

Yarnitsky, D., Sprecher, E., Zaslansky, R., and Hemli, J. A., 1995, "Heat Pain Thresholds: Normative Data and Repeatability," Pain, 60(3), pp. 329-332.

Martin, N. A., and Falder, S., 2017, "A Review of the Evidence for Threshold of Burn Injury," Burns, 43(8), pp. 1624-1639.

Dewey, W. C., 2009, "Arrhenius Relationships From the Molecule and Cell to the Clinic," Int. J. Hyperth., 25(1), pp. 3-20.

Diller, K. R., 2006, "Adapting Adult Scald Safety Standards to Children," J. Burn Care Res., 27(3), pp. 314-322.

ASTM, 2010, "Standard Test Method for Peel Adhesion of Pressure-Sensitive Tape," ASTM, West Conshohocken, PA, Standard No. D3330/D330M.

(56) References Cited

OTHER PUBLICATIONS

Okabe, T., Fujimura, T., Okajima, J., Aiba, S., and Maruyama, S., 2018, "Non-Invasive Measurement of Effective Thermal Conductivity of Human Skin With a Guard-Heated Thermistor Probe," Int. J. Heat Mass Transfer, 126, pp. 625-635.
Lumileds Holding B.V., 2018, "LUXEON IR Domed Line Specification Data," Lumileds Holding B.V., San Jose, CA, accessed Nov. 6, 2019, https://www.lumileds.com/uploads/685/DS191-pdf.
Okada, T., Ishige, R., and Ando, S., 2016, "Analysis of Thermal Radiation Properties of Polyimide and Polymeric Materials Based on ATR-IR Spectroscopy," J. Photopolym. Sci. Technol., 29(2), pp. 251-254.
Weinstein, S., and Hagle, M. E., 2014, Plumer's Principles & Practice of Infusion Therapy, Lippincott Williams & Wilkins, Philadelphia, PA, pp. 320-321.
Henriques, F. C., 1947, "Studies of Thermal Injury—V: The Predictability and the Significance of Thermally Induced Rate Processes Leading to Irreversible Epidermal Injury," Am. J. Pathol., 43(5), pp. 489-502.
ASTM, 2014, "Standard Guide for Heated System Surface Conditions that Produce Contact Burn Injuries," ASTM, West Conshohocken, PA, Standard No. ASTM-C1055-03.
Moon et al., "Evaluation of temperature-dependent adhesive performance via combinatorial probe tack measurements," Feb. 2005, https://aip.scitation.org/doi/abs/10.1063/1.1906105.
Stokes-Griffin et al., "A combined optical-thermal model for near-infrared laser heating of thermoplastic composites in an automated tape placement process," Aug. 2015, https://www.sciencedirect.coni/science/article/abs/pii/S1359835X14002395.
Stansbury et al., "Determination of double bond conversion in dental resins by near infrared spectroscopy," Jan. 2001, https://www.sciencedirect.com/science/article/abs/pii/S0109564100000622.
Kajtna et al., The influence of the polymerization on properties of an ethylacrylate/2-ethyl hexylacrylate pressure-sensitive adhesive suspension, International Journal of Adhesion and Ashesives, vol. 28, Issue 7, Oct. 2008, pp. 382-390.
Kajtna et al., "The Role of Components in Waterbased Microsphere Acrylic Psa Adhesive Properties," Dec. 20, 2006, Mactromelecular Symposia 243(1): 132-146.
Zhang et al., "Repositionable pressure-sensitive adhesive possessing thermal-stimuli switchable transparency," Journal of Materials Chemistry C, Issue 6, 2013.
Hilton et al., "Laser Welding of Fabrics Using Infrared Absorbing Dyes," International Conference on Joining of Advanced and Specialty Materials III ASM 2000, Oct. 9-12, 2000, 6 pages.
Svanevik, "Testing and Improving the UnTape Medical Device Concept," University of Washington, 2018, 91 pages.
International Preliminary Report on Patentability with Written Opinion dated May 29, 2018, for International Application No. PCT/US2016/063156, filed Nov. 21, 2016, 8 pages.
Soifer et al., "Prevention of Peripheral Venous Catheter Complications With an Intravenous Therapy Team," Arch. Intern. Med. 1998, vol. 158, Mar. 9, 1998, pp. 473-477.
O'Grady et al., "Guidelines for the Prevention of Intravascular Catheter-Related Infections," Prevention Guidelines for Catheter-Related Infections, Clinical Infectious Diseases 2002, vol. 35, Dec. 1, 2002, pp. 1281-1307.
Bregenzer et al., "Is Routine Replacement of Peripheral Intravenous Catheters Necessary?" Arch. Intern. Med. 1998, vol. 158, Jan. 26, 1998, pp. 151-156.
Miller et al., "Reduction in Nosocomial Intravenous Device-Related Bacteremias After Institution of an Intravenous Therapy Team," Journal of Intravenous Nursing, vol. 19, No. 2, Mar./Apr. 1996, pp. 103-106.
Karwoski et al., "Experiments on peeling adhesive tapes from human forearms," Skin Research and Technology, 2004, vol. 10, pp. 271-277.
Muralidharan et al., "Ncm, a Photolabile Group for Preparation of Caged Molecules: Synthesis and Biological Application," PLoS One 11(10): DOI:10.1371/journal.pone.0163937, 2016, pp. 1-22.
Ungar et al., "A New Approach to Defining Human Touch Temperature Standards," NASA/Johnson Space Center, pp. 1-10.
Wegner et al., "Photocleavable linker for the patterning of bioactive molecules," Scientific Reports, 5, 18309, DOI: 10.1038/srep18309, Dec. 16, 2015, pp. 1-7.
Rio et al., "Modulating the electronic properties of porphyrinoids: a voyage from the violet to the infrared regions of the electromagnetic spectrum," Organic & Biomolecular Chemistry, 2008, vol. 6, pp. 1877-1894.
Çakir et al., "Water soluble {2-[3-(diethylamino)phenoxy]ethoxy} substituted zinc(II) phthalocyanine photosensitizers," Journal of Luminescence, 159 (2015), pp. 79-87.

PHOTOSENSITIVE MEDICAL TAPE

CROSS-REFERENCE TO RELATED APPLICATIONS

This application is a 371 of International Application No. PCT/US2016/063156, filed Nov. 21, 2016, which claims the benefit of U.S. Provisional Application No. 62/259,535, filed on Nov. 24, 2015, the contents of which are incorporated herein by reference.

TECHNICAL FIELD

This disclosure relates generally to medical tape, and in particular but not exclusively, relates to photosensitive medical tape.

BACKGROUND INFORMATION

In medicine, a peripheral venous catheter (PVC, peripheral intravenous catheter or PIV, peripheral venous line, or peripheral venous access catheter) is a catheter placed into a peripheral vein in order to administer medication or fluids. Upon insertion, the PVC can also be used to draw blood.

A PVC is the most commonly used vascular access in medicine. It is given to most emergency room and surgical patients, and before some radiological imaging techniques in order to administer radiocontrast, for example. In the United States, more than 25 million patients get a PVC each year.

A PVC is typically placed in a vein on the hand or arm and secured by a catheter securement device or pressure-sensitive adhesive tape and a clear polyether/polyurethane film. However, the Centers for Disease Control and Prevention advise in their guidelines that the PVC needs to be replaced every 96 hours in order to minimize infection risk at the insertion site.

Medical adhesive-related skin injury (MARSI) is a recognized complication of removing adhesive from skin. The strength of the adhesive can remove dead skin cells to separating fragile skin layers and cause injury.

Current available adhesive products are pressure-sensitive. Removal of pressure-sensitive adhesive products and catheter securement devices require a combination of technique and use of a solvent to disrupt the adhesive connection with the skin or the backing.

BRIEF DESCRIPTION OF THE DRAWINGS

Non-limiting and non-exhaustive examples of the invention are described with reference to the following figures, wherein like reference numerals refer to like parts throughout the various views unless otherwise specified.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

Examples of an apparatus, system, and method for photosensitive medical tape are described herein. In the following description, numerous specific details are set forth to provide a thorough understanding of the examples. One skilled in the relevant art will recognize; however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one example" or "one embodiment" means that a particular feature, structure, or characteristic described in connection with the example is included in at least one example of the present invention. Thus, the appearances of the phrases "in one example" or "in one embodiment" in various places throughout this specification are not necessarily all referring to the same example. Furthermore, the particular features, structures, or characteristics may be combined in any suitable manner in one or more examples.

Figure 1:
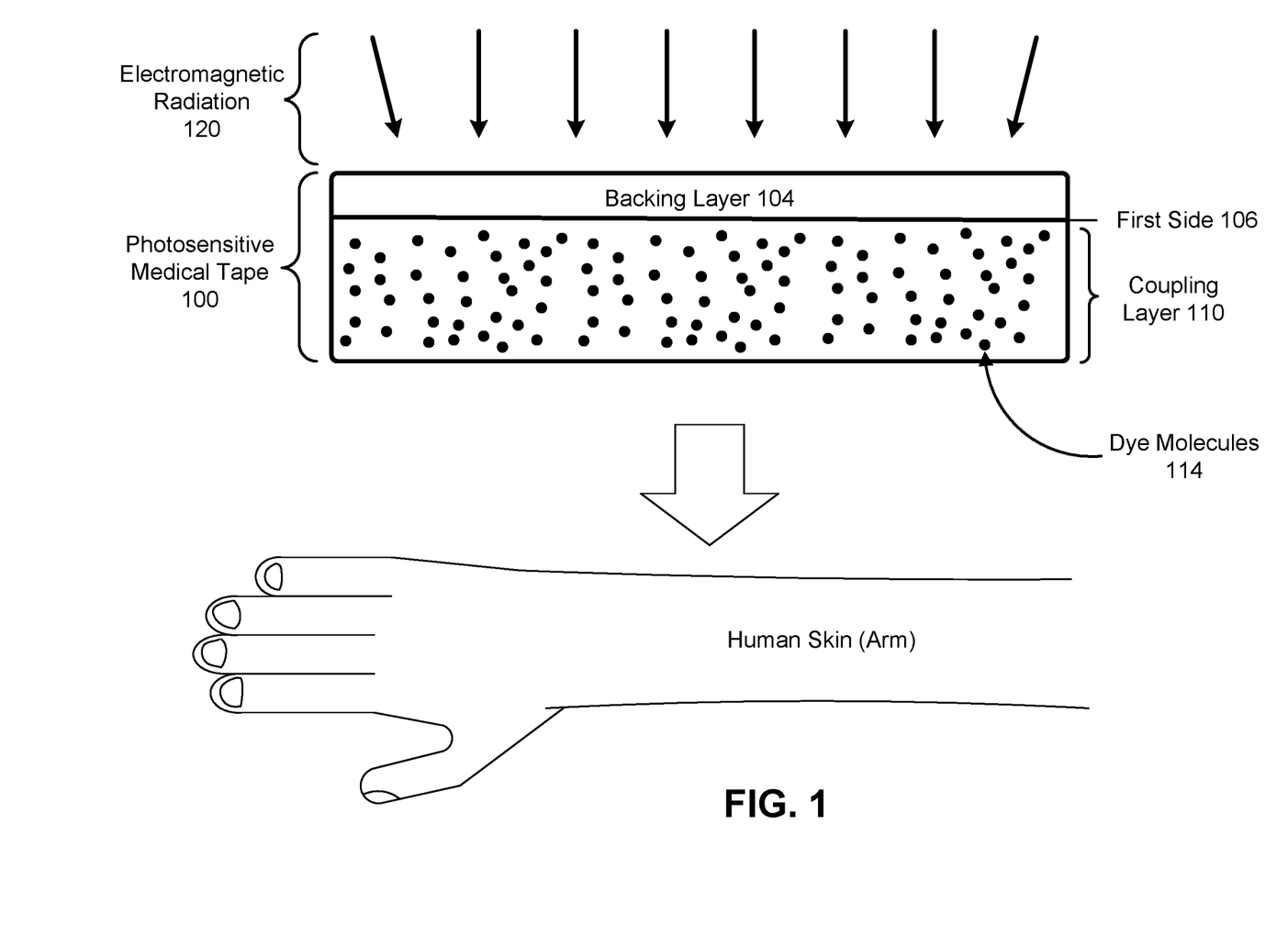
FIG. 1 is a cross sectional illustration of an example photosensitive medical tape, in accordance with the teachings of the present invention.

FIG. 1 is a cross sectional illustration of an example photosensitive medical tape 100. Photosensitive medical tape 100 includes backing layer 104 (having a first side 106), coupling layer 110, and plurality of dye molecules 114.

As illustrated, photosensitive medical tape 100 includes coupling layer 110 disposed on first side 106 of backing layer 104 to provide adhesion of photosensitive medical tape 100 to the human skin (e.g., the arm depicted). Photosensitive medical tape 100 is flexible to allow conformity to the surface of attachment, such as human skin or a medical device. Backing layer 104 is at least partially transparent to a first spectrum of electromagnetic radiation 120. Photosensitive medical tape 100 is disposed to absorb a second spectrum of electromagnetic radiation 120 to decrease the toughness or tensile strength of the adhesion provided by coupling layer 110. Thus allowing photosensitive medical tape 100 to be easily removed from human skin (or other objects such as a peripheral venous catheter, tubes, needles, the tape itself, and other medical devices). Embodiments are also applicable to non-human subjects, such as animals with fur and other veterinary subjects.

In one example, backing layer 104 and coupling layer 110 of photosensitive medical tape 100 are relatively thick layers having a thickness of several microns to millimeters. Coupling layer 110 may provide adhesion due to the material composition of the coupling layer. For example, coupling layer 110 may include an acrylic adhesive component to provide adhesive properties. In other examples, coupling layer 110 may include a plurality of different components having adhesive properties. The coupling layer 110 may be a mixture of different adhesive components or may be layers of the same or different adhesive components. The composition of coupling layer 110 may be based, at least in part, on the desired material properties, such as biocompatibility, glass transition temperature, optical properties, adhesive properties, etc.

In another example, backing layer 104 may include a compensating dye or colorant to adjust the transparency of backing layer 104 to the first spectrum of electromagnetic radiation 120. The compensating dye or colorant may flatten the reflectance (i.e., make the plastic appear without a color bias) across the visible spectrum of electromagnetic radiation to improve color fidelity.

In the illustrated example, photosensitive medical tape 100 includes plurality of dye molecules 114 dispersed in coupling layer 110. Plurality of dye molecules 114 may absorb at least a portion of the second spectrum of electromagnetic radiation 120. Upon absorption of the second spectrum of electromagnetic radiation 120, an increase in temperature in at least part of the photosensitive medical tape 100 may occur. The increase in temperature may result in a decrease in strength of the adhesion provided by coupling layer 110. In one example, the increase in temperature of photosensitive medical tape 100 causes the temperature of at least part of coupling layer 110 to reach or exceed the glass transition temperature of coupling layer 110. The part of coupling layer 110 near or above the glass transition temperature has significantly reduced adhesive properties relative to the part of coupling layer 110 at room temperature or below the glass transition temperature.

In the illustrated example, backing layer 104 may be at least partially transparent to a first spectrum of electromagnetic radiation 120. The first spectrum of electromagnetic radiation 120 may include the visible spectrum to increase visibility of the underlying coupling layer 110. Coupling layer 110 may also be partially transparent to the visible spectrum to increase visibility of the underlying human skin or medical device in contact with photosensitive medical tape 100. The first spectrum of electromagnetic radiation 120 may also include the second spectrum of electromagnetic radiation that is absorbed by photosensitive medical tape 100. The second spectrum of electromagnetic radiation may propagate through the backing layer 104 and subsequently be absorbed by plurality of dye molecules 114 dispersed in coupling layer 110. The second spectrum of electromagnetic radiation may be in the near infra-red (NIR) or infra-red (IR) range such that the plurality of dye molecules 114 are NIR or IR absorbing molecules. Example frequency ranges for NIR or IR ranges include one or more of 800-1000 nanometers. Example sources may include Epolight 3169 (Epolin, Newark, N.J.) with absorbance peak at 940 nm which can match high power NIR LED illumination light sources. Other examples are 700-900 nm using Epolight 3442 with peak absorbance at 810 nm, or 800-1100 nm using Epolight 3832 (Epolin, Newark, N.J.) with IR peak absorbance at 960 nm. Surface coating IR absorbing dye molecules can be Clearweld 900 series product from Crysta-Lyn Chemical Company (Binghamton, N.Y.).

Plurality of dye molecules 114 may be NIR absorbing molecules or complexes and may be transparent to, or have a low absorbance to, frequencies of electromagnetic radiation outside the NIR or IR regime. For example, the dye molecules could be bound inside a polystyrene microsphere for improved compatibility to the host polymer material or biocompatibility. In some examples, other energy absorbing particles that absorb a particular frequency of electromagnetic radiation are used in place of, or in addition to, plurality of dye molecules 114. Energy absorbing particles include ultra-violet (UV) spectrum absorbing dye molecules or complexes that may be coupled to the surface of photosensitive medical tape 100 or backing layer 104. Energy absorbing particles may also include a plurality of photoactive molecules or a plurality of photocleavable dye molecules. Photocleavable dye molecules absorb near UV light just at or below the shortest wavelength of visible light. Energy absorbing particles may be molecules, complexes, filaments, or nanoparticles. Energy absorbing particles may also include metal nanoparticles having a size that can be adjusted to absorb a specific range of energy of electromagnetic radiation.

As illustrated, energy absorbing particles, such as plurality of dye molecules 114, are dispersed within coupling layer 110. In some examples, plurality of dye molecules 114 is dispersed in at least one of backing layer 104, coupling layer 110, or a sacrificial thin film disposed in coupling layer 110 in contact with backing layer 104. In the illustrated example, the concentration of plurality of dye molecules 114 is uniform throughout coupling layer 110, meaning the concentration of plurality of dye molecules 114 is similar or substantially the same throughout the length and thickness of coupling layer 110. In other examples, the distribution or concentration of plurality of dye molecules 114 is non-uniform. In one example, coupling layer 110 is manufactured using a simple method of mixing the particles within the coupling layer material and casting, rolling, or stretching it to achieve a layer.

Figure 2A:
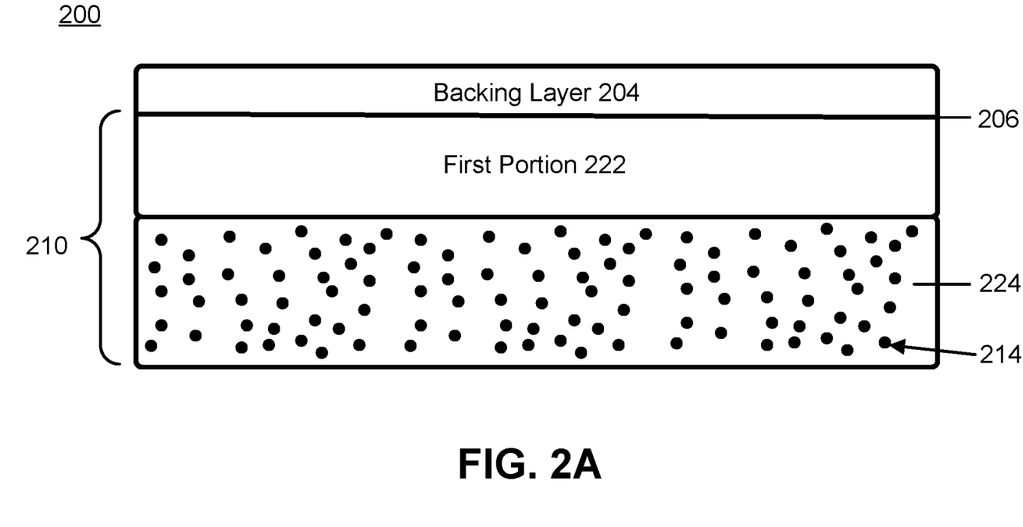
FIGS. 2A-2B are cross sectional illustrations of example photosensitive medical tape, in accordance with the teachings of the present invention.

FIG. 2A illustrates an example of photosensitive medical tape 200 which includes backing layer 204, coupling layer 210, and plurality of dye molecules 214. Coupling layer 210 is disposed on first side 206 of backing layer 204. Photosensitive medical tape 200 is similar to photosensitive medical tape 100; however, the one difference is first portion 222 of coupling layer 210 proximate to backing layer 204 has a glass transition temperature that is greater than a glass transition temperature of second portion 224 of coupling layer 210. The individual material composition of first portion 222 and second portion 224 of coupling layer 210 contributes to the overall glass transition temperature of each respective portion.

In one example, upon an increase of temperature from the absorption of the second spectrum of electromagnetic radiation, at least part of coupling layer 210 softens significantly due to reaching the glass transition temperature of coupling layer 210. If the temperature increase is transient, then the glass transition temperature can be much higher. The shorter the time the human skin is heated or contacted, the higher the glass transition temperature can be. Furthermore, if the human skin is thermally insulated, then a higher glass transition temperature can be allowed and/or tolerated by the patient.

In another example, insulating of the human skin can be provided by having a greater distance between plurality of dye molecules 214 and pain sensors in the human skin. Alternatively, or additionally, air in coupling layer 210 that is in contact with the human skin may also further thermally insulate the human skin. The addition of a numbing agent to coupling layer 210 or a swab of disinfectant applied to the human skin before attachment of photosensitive medical tape 200 may also further protect the human skin. In one example, lidocaine mixed with a disinfectant swap may be applied to the human skin. The disinfectant may be iodine or equivalent as an active agent. In another example, a barrier film, cream, or lotion may also be applied to the human skin before attachment of photosensitive medical tape 200. The barrier film, cream, or lotion may include at least one of a disinfectant, a numbing agent, and an electromagnetic radiation blocker such as a UV or IR blocker. In another example, the photosensitive medical tape may be at least one of hypo allergenic, latex free, and semi-permeable.

In the illustrated example, second portion 224 may include plurality of dye molecules 214. Plurality of dye molecules 214 may be dispersed uniformly throughout second portion 224. First portion 222 may include no dye molecules. In another example, plurality of dye molecules 214 may be dispersed uniformly throughout first portion 222 and second portion 224 of coupling layer 210. In yet another example, plurality of dye molecules 214 may be dispersed uniformly throughout first portion 222 but not second portion 224 of coupling layer 210.

In one example, plurality of dye molecules 214 have an absorbance of near infra-red light of nearly ninety percent and nearly zero percent or 5% to 25% optical attenuation for other ranges of electromagnetic radiation. In another example, backing layer 204 may reflect up to eighty to ninety percent of incident electromagnetic radiation in or across the infra-red and thermal range of electromagnetic radiation. In yet another example, backing layer 204 may transmit nearly eighty percent of the visible spectrum of electromagnetic radiation. The transmittance of backing layer 204 for other ranges of electromagnetic radiation may depend on the functionality required for backing layer 204 or coupling layer 210 underneath. Backing layer 204 may include a highly reflecting thin layer on an external side to reflect near infra-red and beyond portions of the electromagnetic radiation.

Figure 2B:
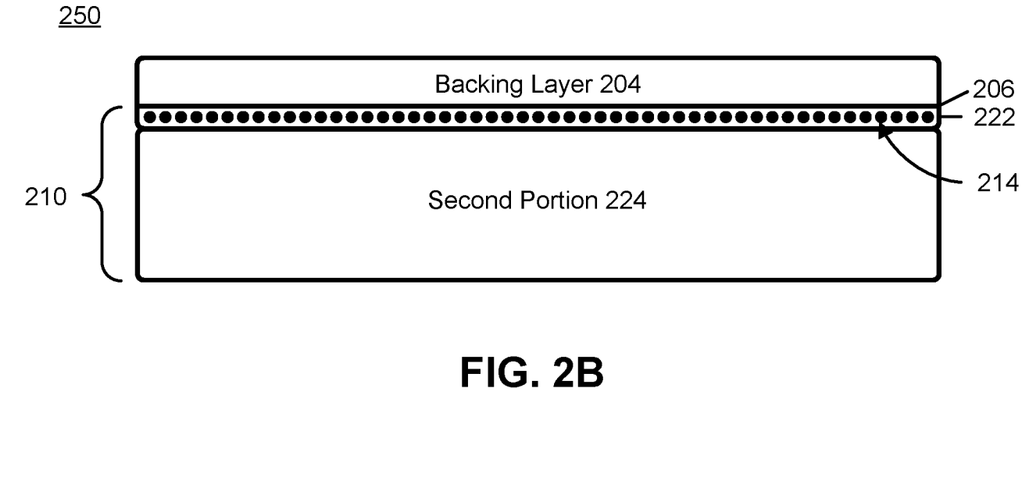

FIG. 2B illustrates an example photosensitive medical tape 250 and includes backing layer 204, coupling layer 210, and plurality of dye molecules 214. Coupling layer 210 is disposed on first side 206 of backing layer 204. First portion 222 of coupling layer 210 is disposed between backing layer 204 and second portion 224 of the coupling layer 210. Photosensitive medical tape 250 is similar to photosensitive medical tape 200. But one difference is plurality of dye molecules 214 is disposed in first portion 222 of the coupling layer 210 in contact with backing layer 204. First portion 222 of coupling layer 210 is a thin film and is between a monolayer thick to several millimeters thick. In one example, the thickness of first portion 222 is the same as a dimension of an individual dye molecule in plurality of dye molecules 214.

In another example, a plurality of photoactive molecules are included in place of, or in addition to, plurality of dye molecules 214. Coupling layer 210 may include a plurality of photoactive molecules, where upon absorption of the second spectrum of electromagnetic radiation, the plurality of photoactive molecules initiate a chemical reaction within coupling layer 210 to decrease the strength of the adhesion provided by coupling layer 210. The chemical reaction initiated by the plurality of photoactive molecules may result in degradation of the mechanical and/or adhesive properties of first portion 222 of coupling layer 210.

In yet another example, the plurality of photoactive molecules may include nitrobenzyl or modified nitrobenzyl molecules or complexes that have a peak absorbance at an electromagnetic radiation wavelength of 260 nm or 365 nm.

In another example, the chemical reaction initiated by the photoactive molecules may be photocleavage. Typically, higher energy photons in the UV range are absorbed by the plurality of photoactive molecules. The plurality of photoactive molecules may include photoinitiators, photosensitizers, or photoactivator molecules. The plurality of photoactive molecules may absorb the second spectrum of electromagnetic radiation and release free radicals that cut or degrade the mechanical or adhesive properties of photosensitive medical tape 250. Thus allowing for the easy release of photosensitive medical tape 250 from human skin.

In one example, photosensitive medical tape 250 may be manufactured using a sputtering process or other known thin film deposition techniques. The manufacturing of photosensitive medical tape 250 may be integrated into roll-to-roll manufacturing. Other techniques such as spray coating, bulking dispensing with mechanical or thermal assistance, solvent assisted application of coupling layer 210, or admixture of light absorbing materials into coupling layer 210 may also be used.

Figure 3:
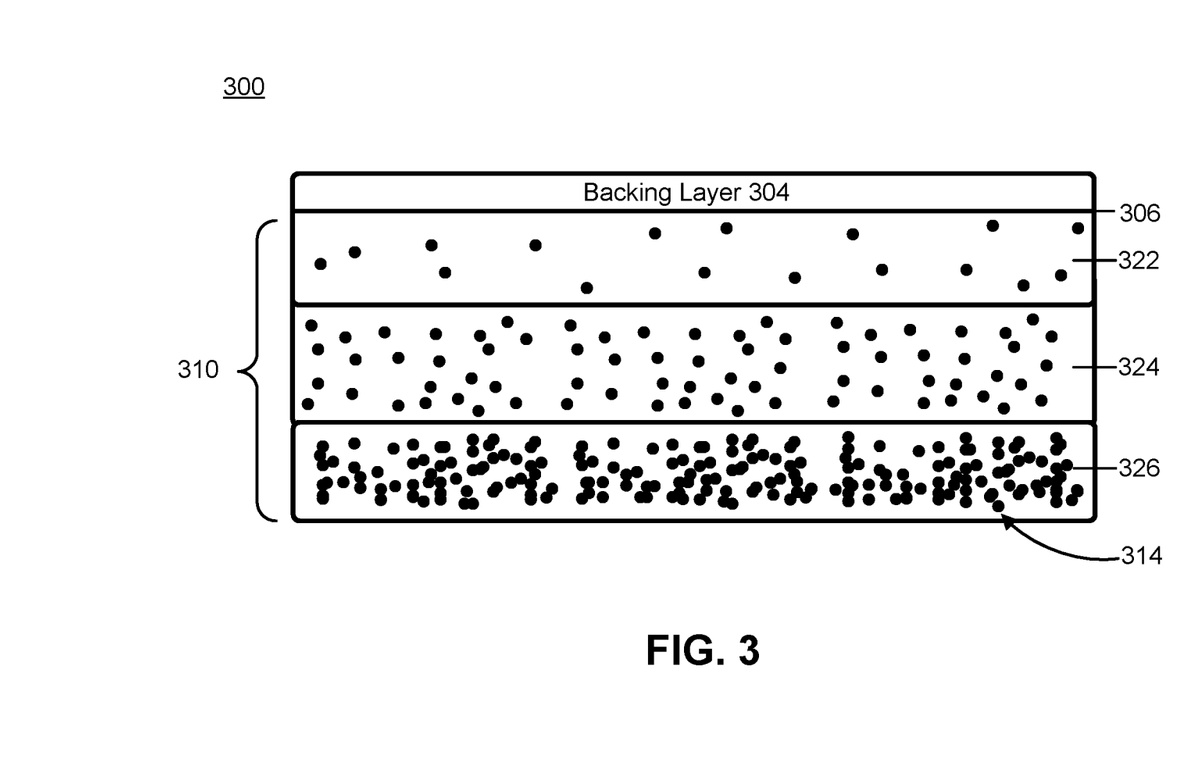
FIG. 3 is a cross sectional illustration of an example photosensitive medical tape, in accordance with the teachings of the present invention.

FIG. 3 illustrates an example photosensitive medical tape 300 and includes backing layer 304, coupling layer 310, and plurality of energy absorbing particles, such as plurality of dye molecules 314. The coupling layer 310 is disposed on a first side 306 of backing layer 304. Photosensitive medical tape 300 is similar to photosensitive medical tape 200. However, one difference is a concentration of the plurality of dye molecules 314 increases as a step function in a direction away from backing layer 304.

In the illustrated example, plurality of dye molecules 314 are dispersed within first portion 322, second portion 324, and third portion 326 of coupling layer 310. The concentration of plurality of dye molecules 314 is uniform within each first portion 322, second portion 324, and third portion 326 of coupling layer 310. The concentration of plurality of dye molecules 314 in first portion 322, second portion 324, and third portion 326 is different from each other such that the concentration of plurality of dye molecules 314 increases in a direction away from backing layer 304. In another example, the concentration of plurality of dye molecules 314 within first portion 322, second portion 324, and third portion 326 may increase towards backing layer 304. In yet another example, a plurality of portions of coupling layer 310 each have a uniform concentration of plurality of dye molecules 314.

The spatial organization of energy absorbing particles, such as plurality of dye molecules 314, can be fabricated by stacking multiple layers together. Stacking these layers together may change glass transition properties or other mechanical properties. In particular, a function of stacking multiple layers is to provide spatially distributed energy absorbing properties in photosensitive tape 300. In one example, multiple portions of coupling layer 310 can be constructed from the same type of material, for example an acrylate adhesive, but at different energy absorbing particle concentrations for each layer.

Figure 4A:
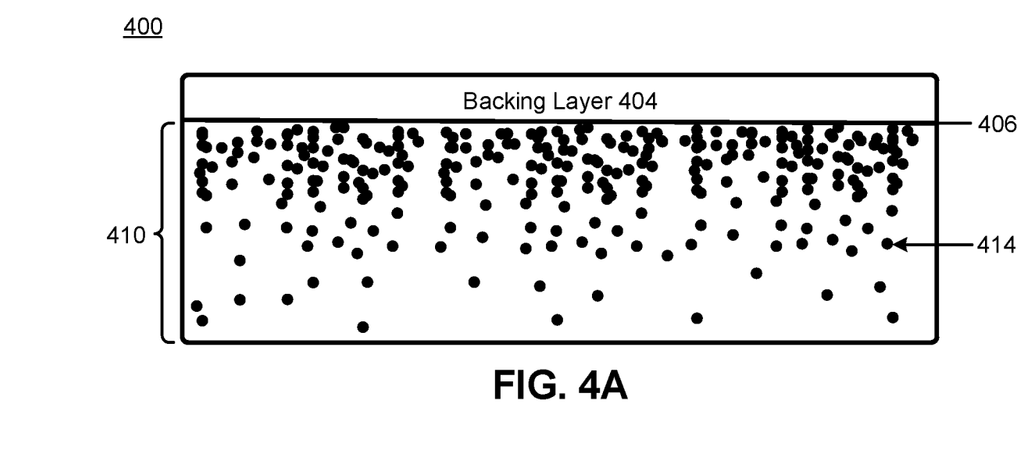
FIGS. 4A-4B are cross sectional illustrations of example photosensitive medical tape, in accordance with the teachings of the present invention.

FIG. 4A illustrates an example photosensitive medical tape 400 and includes backing layer 404, coupling layer 410, and plurality of energy absorbing particles, such as plurality of dye molecules 414. The coupling layer 410 is disposed on first side 406 of backing layer 404. Photosensitive medical tape 400 is similar to photosensitive medical tape 200, but one difference is plurality of dye molecules 414 is dispersed non-linearly within coupling layer 410. In the illustrated example, the concentration of plurality of dye molecules 414 exponentially increases towards backing layer 404 such that a majority of plurality of dye molecules 414 is proximate to backing layer 404.

Figure 4B:
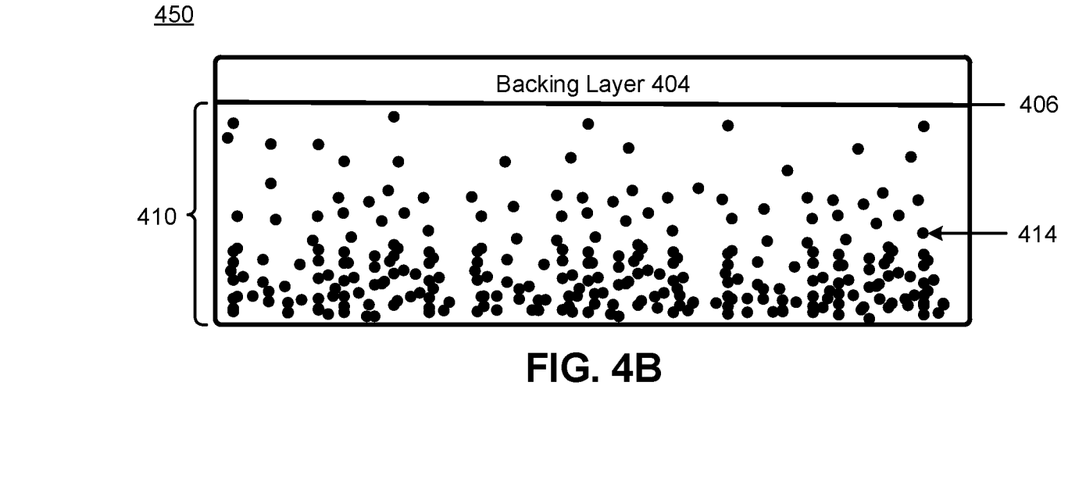

FIG. 4B illustrates an example photosensitive medical tape 450. Photosensitive medical tape 450 is similar to photosensitive medical tape 400. One difference is the concentration of plurality of dye molecules 414 exponentially decreases towards backing layer 404 such that a majority of plurality of dye molecules 414 is proximate to a side of coupling layer 410 not attached to backing layer 404.

The non-linear concentration of plurality of dye molecules 414 dispersed within coupling layer 410 forms a gradient of plurality of dye molecules 414. In one example, gradients of the energy absorbing particles, such as plurality of dye molecules 414, can be concentrated near backing layer 404 so that the interface softens preferentially. In another example, the plurality of dye molecules 414 is concentrated near human skin or at a contact surface of photosensitive medical tape 450 so substantially all of photosensitive medical tape 450 can be removed easily and quickly when energy is applied or absorbed. The gradients can be manufactured by solvent swelling and absorption into the porous sponge-like temporary state of coupling layer 410. In a subsequent drying step the solvent is removed from coupling layer 410 leaving behind the non-volatile dye particles.

Figure 5:
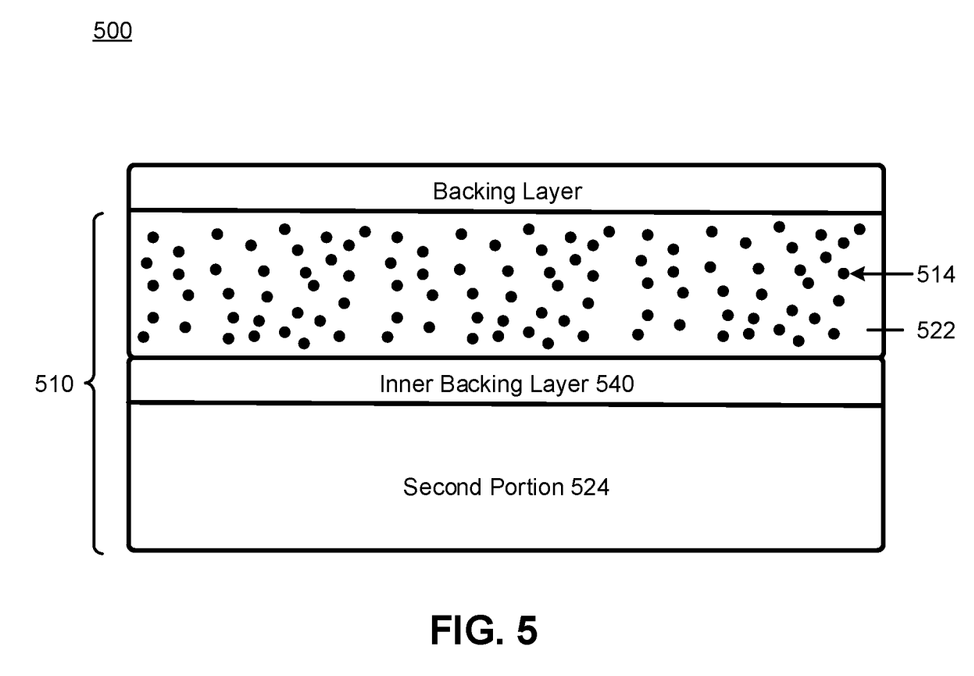
FIG. 5 is a cross sectional illustration of an example photosensitive medical tape, in accordance with the teachings of the present invention.

FIG. 5 illustrates an example photosensitive medical tape 500. Photosensitive medical tape 500 is similar to photosensitive medical tape 200; however, one difference is inner backing layer 540 is disposed between first portion 522 and second portion 524 of coupling layer 510, and second portion 524 of coupling layer 510 adheres to the human skin. Plurality of dye molecules 514 are uniformly dispersed throughout a thickness of first portion 522 of the coupling layer 510. In other examples, plurality of dye molecules 514 may be dispersed throughout first portion 522, second portion 524, or both first portion 522 and second portion 524 of coupling layer 510. Plurality of dye molecules 514 may be dispersed uniformly or may have a non-linear concentration throughout the thickness of either first portion 522 or second portion 524 of coupling layer 510.

Figure 6A:
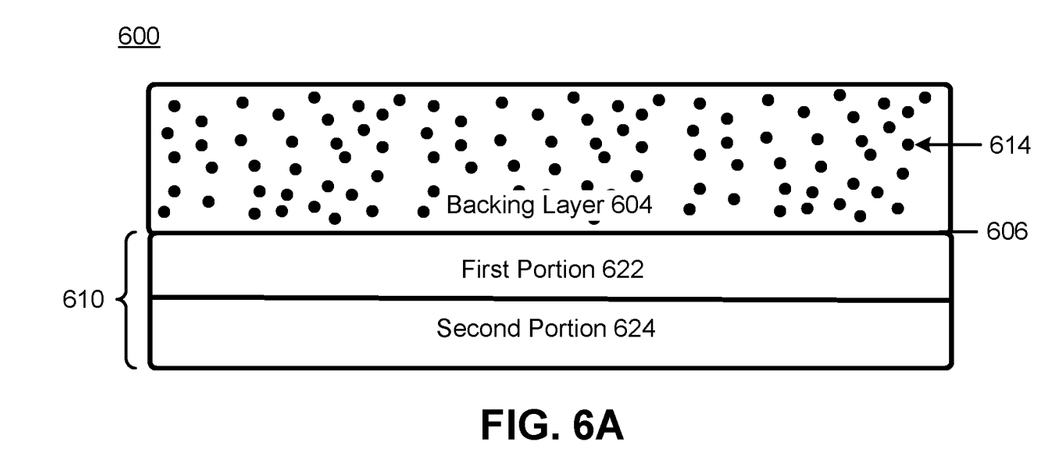
FIGS. 6A-6B are cross sectional illustrations of example photosensitive medical tape, in accordance with the teachings of the present invention.

FIG. 6A illustrates an example of photosensitive medical tape 600 which includes backing layer 604, coupling layer 610, and plurality of dye molecules 614. Coupling layer 610 is disposed on first side 606 of backing layer 604. Photosensitive medical tape 600 is similar to photosensitive medical tape 200; however, one difference is that plurality of dye molecules 614 is dispersed within backing layer 604.

Similar to tape 200, a first portion 622 of coupling layer 610 proximate to backing layer 604 has a glass transition temperature that is greater than a glass transition temperature of second portion 624 of coupling layer 610. The individual material composition of first portion 622 and second portion 624 of coupling layer 610 contributes to the overall glass transition temperature of each respective portion.

In one example, upon an increase of temperature from the absorption of the second spectrum of electromagnetic radiation, at least part of coupling layer 610 softens significantly due to reaching the glass transition temperature of coupling layer 610.

In the illustrated example, backing layer 604 may include plurality of dye molecules 614. Plurality of dye molecules 614 may be dispersed uniformly throughout backing layer 604. First portion 622 and second portion 624 may include no dye molecules. In another example, plurality of dye molecules 614 may be dispersed uniformly throughout first portion 622 and second portion 624 of coupling layer 610. In yet another example, plurality of dye molecules 614 may be dispersed uniformly throughout first portion 622 but not second portion 624 of coupling layer 610. The backing layer 604, for example polyurethane or other transparent plastic film, can be dyed with the IR/NIR dye(s) using dye-in-polymer technology, which may include blending into raw polymer during fabrication. In some examples, backing layer 604 may be a semi-porous film that has breathable properties such that oxygen can be transmitted through the film and reach the skin and excess skin moisture can evaporate. Therefore, woven or mesh type polymer fibers often comprise backing layer 604.

Figure 6B:
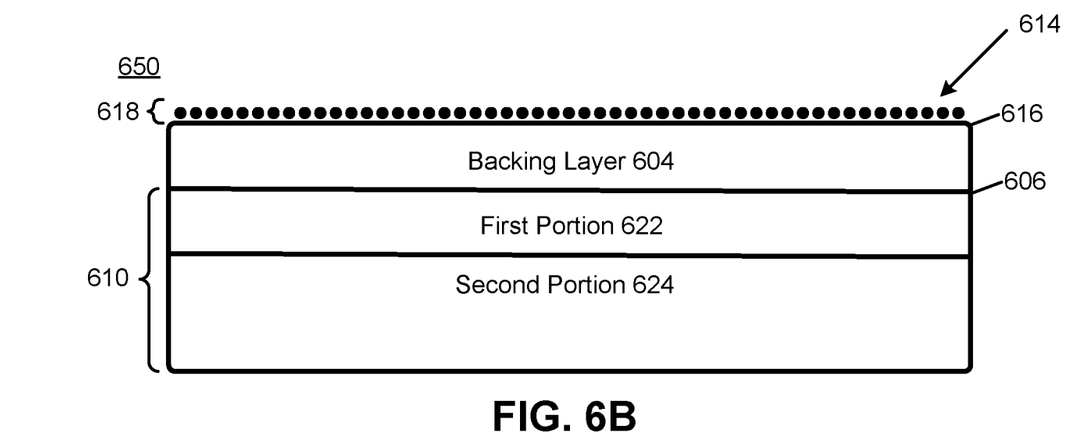

FIG. 6B illustrates an example photosensitive medical tape 650 and includes backing layer 604, coupling layer 610, and plurality of dye molecules 614. Coupling layer 610 is disposed on first side 606 of backing layer 604. First portion 622 of coupling layer 610 is disposed between backing layer 604 and second portion 624 of the coupling layer 610. Photosensitive medical tape 650 is similar to photosensitive medical tape 250. But one difference is plurality of dye molecules 614 is disposed on a second side 616 of the backing layer, opposite the first side of backing layer 604. The plurality of dye molecules 614 may be provided on second side 616 as a coating or a thin film 618 and may be between a monolayer thick to several millimeters thick. In one example, the thickness of the coating or film 618 is the same as a dimension of an individual dye molecule or encapsulated dye molecules in microspheres in plurality of dye molecules or encapsulated dye molecules 614 in microspheres. The coating or film may be also be transparent and thin, such as a few thousandths of an inch thick, e.g. 0.005".

In both tapes 600 and 650, the plurality of dye molecules 614, which cause a temperature increase upon application of the second spectrum, may be physically separated from a layer or a portion of a layer responsive to the temperature increase. For example, the second portion 624 of coupling layer 610 is separated from the backing layer 604 in tape 600 by first portion 622 of the coupling layer 610. The second portion 624 of the coupling layer 610 is separated from coating or film 618 in tape 650 by the backing layer 604 and the first portion 622 of the coupling layer 610. In such embodiments, the intermediate layers may have none of the plurality of dye molecules dispersed therein. The intermediate layers may also be non-reactive to temperature changes caused by the plurality of dye molecules 614, and have glass transition temperatures that are significantly higher than that of the second portion 624 or first portion 622 and second portion 624. For example the lower glass transition temperature may include temperatures greater than 110 degrees F. or above 150 degree F. For example, the higher glass transition temperature may include temperatures greater than 130 degrees Fahrenheit. Transient heating and removal procedures may allow transition temperatures above this value, such as 180 degrees Fahrenheit. Each of the layers in tapes 600, 650 may also be transparent to the visible spectrum. The advantages of such features and arrangements are discussed elsewhere herein. In one example, photosensitive medical tape 650 may be manufactured using a sputtering process or other known thin film deposition techniques. For example, the backing layer 604 may include polyurethane or other transparent plastic film, spray coated on first and/or second sides 606,616 with the plurality of dye molecules 614.

Further embodiments may also include a combination of features shown in FIG. 6A and FIG. 6B. For example, one such embodiment may include a backing layer 604 impregnated with plurality of dye molecules 614 and a film coating 618 with a second plurality of dye molecules 614 provided on a second surface 616 of the same backing layer 604. Similar to FIG. 6A and FIG. 6B, the first portion 622 or the second portion 624 may be reactive to a change in temperature associated with the plurality of dye molecules 614.

The examples of photosensitive medical tape described above may also be part of a system comprising the photosensitive medical tape and a light source to generate the second spectrum of electromagnetic radiation.

Figure 7A:
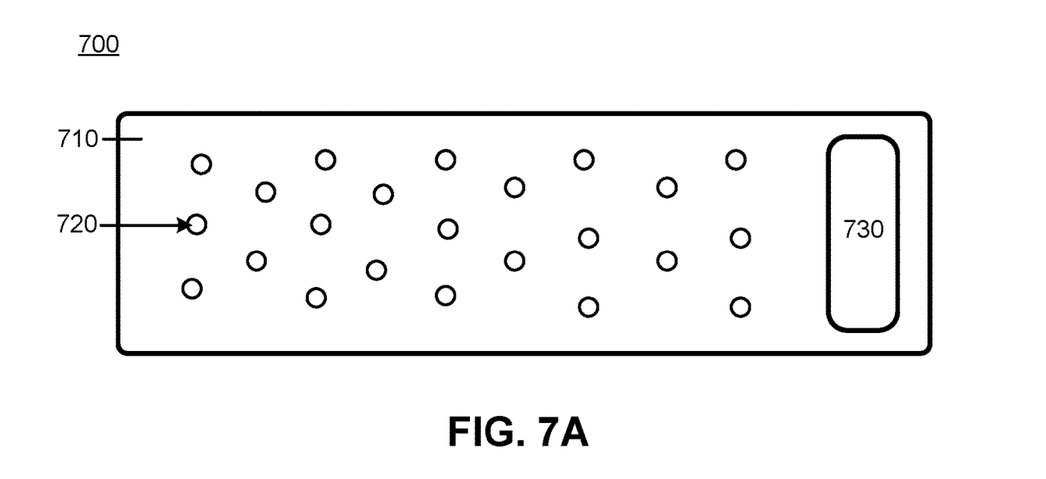
FIGS. 7A-7C illustrate an example light source for the system including the photosensitive medical tape illustrated in FIGS. 1-6, in accordance with the teachings of the present invention.

FIG. 7A illustrates an example arm sleeve 700 including first side 710, plurality of light sources 720, and connector 730. Arm sleeve 700 is wrapped around an arm that has photosensitive medical tape attached. First side 710 may be opaque or reflective. Plurality of light sources 720 may include a light source to generate a second spectrum of electromagnetic radiation. The generated second spectrum of electromagnetic radiation may be directed to the above described examples of photosensitive medical tape. Connector 730 allows for arm sleeve 700 to attach to itself such that the generated second spectrum of electromagnetic radiation is confined to within the enclosure of arm sleeve 700. In one example connector 730 is Velcro. The arm sleeve 700 may be four to ten inches long to sufficiently allow for arm sleeve 700 to fully enclose photosensitive medical tape attached to a human arm.

In one example, if the photosensitive medical tape includes a plurality of photoactive or photocleavable molecules, the decrease in strength of the adhesion or decrease in mechanical properties is irreversible. Once the chemical reaction of the photoactive molecule completes, arm sleeve 700 can be removed and photosensitive medical tape can be removed at any time. In one example, the chemical reaction may be a photo-activated reverse catalysis that initiates a softening of the coupling layer.

Figure 7B:
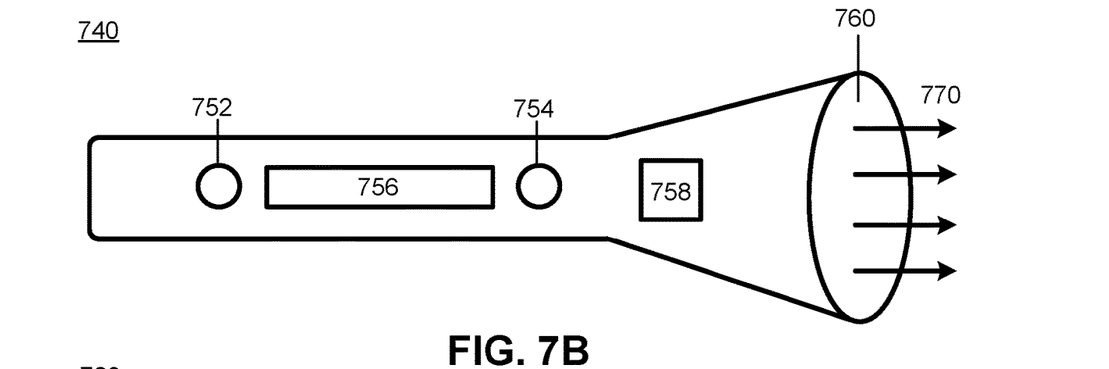

FIG. 7B illustrates an example portable flashlight 740 including first switch 752, second switch 754, power control slider 756, light source 758, and reflector 760. Light source 758 is to generate a second spectrum of electromagnetic radiation 770 to be received by the above described photosensitive medical tape. Reflector 760 reflects the generated second spectrum of electromagnetic radiation such that generated second spectrum of electromagnetic radiation 770 is substantially oriented towards a singular direction. Disposed within flashlight 740 may be batteries to provide power necessary to generate a second spectrum of electromagnetic radiation 770. Power control slider 756 allows for control of intensity of the generated second spectrum of electromagnetic radiation 770. In order to generate the second spectrum of electromagnetic radiation, flashlight 740 may include safety controls including first switch 752 and second switch 754 which need to be pressed or activated at the same time. Pressing just one of first switch 752 or second switch 754 may generate a single range of electromagnetic energy, such as visible light. Visible light may also be a safety feature and user aide. Inclusion of a visible LED into the assembly will alert the operator that the invisible near infrared beam is active. The visible LED can also serve to guide the user to the NIR "hot spot".

In one example light source 758 may generate a spectrum of electromagnetic radiation that includes two or more energy ranges, such as generating NIR and visible light and concurrently delivering the two or more energy ranges to the same location. The output of the two or more energy ranges may be collimated or focused together and can be continuously emitted or pulsed intermittently.

In one example, first switch 752 and second switch 754 must be pressed simultaneously to generate electromagnetic radiation in the red visible regime and the NIR regime. If only first switch 752 or second switch 754 is pushed and both the NIR regime and red visible regime were being emitted previously, flashlight 740 will quickly stop emitting the NIR regime. If only first switch 752 or second switch 754 is pushed, then only the visible regime, such as red or white light, is emitted. This allows flashlight 740 to be used as a multipurpose device for nursing staff since pen lights are already routinely used by nursing staff in hospitals, clinics, nursing centers, or at private homes.

Figure 7C:
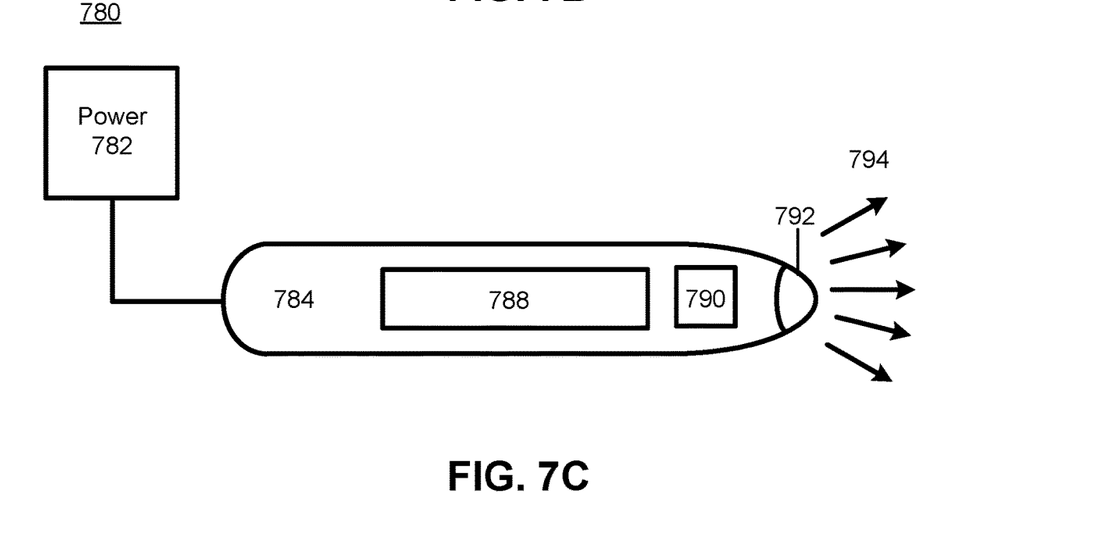

FIG. 7C illustrates an example wand 780 including power source 782, body of the wand 784, battery source 788, and light source 790, and tip of the wand 792. Power source 782 is coupled to the body of the wand 784 and provides power to generate a second spectrum of electromagnetic radiation 794. Disposed within the body of the wand 784 is battery source 788. Battery source 788 may provide a backup power source to generate a second spectrum of electromagnetic radiation 794. Light source 790 is coupled to power source 782 and battery source 788 and generates the second spectrum of electromagnetic radiation 794. Wand 780 may focus the generated second spectrum of electromagnetic radiation 794 at a tip of the wand 792.

In one example wand 780 is rechargeable. In another example, wand 780 is no wider than a highlighter or marker such that wand 780 is easily held in a human hand. Wand 780 may have minimal or no surface crevices for ease of cleaning.

Energy delivery devices such as arm sleeve 700, flashlight 740, and wand 780 can provide the energy necessary for quickly and less forcibly removing photosensitive medical tape, by emitting the second spectrum of electromagnetic radiation. In another example, an incandescent light source or light bulb with specialized gas emission in the specific NIR range can be used to generate the second spectrum of electromagnetic radiation. In another example, a pen light may be used to generate electromagnetic energy in the NIR range with a laser. The laser of the pen light can be diffracted or refracted into a line of illumination to better match the edge of the photosensitive medical tape being pulled up from the human skin or another surface. Similarly, the pen light may emit electromagnetic radiation in both the red visible regime and the NIR regime to ensure a user is aware of which surface is being illuminated.

In another example, rapid removal of the photosensitive medical tape may be achieved by using a high power light source. Upon illumination of the photosensitive medical tape with the high power light source, the high power light source may transiently raise the temperature and soften the coupling layer right before removal or during the removal processing. This light source may be transiently aimed and possibly focused to the point where the tape is being pulled up and back off the skin or device.

Figure 8:
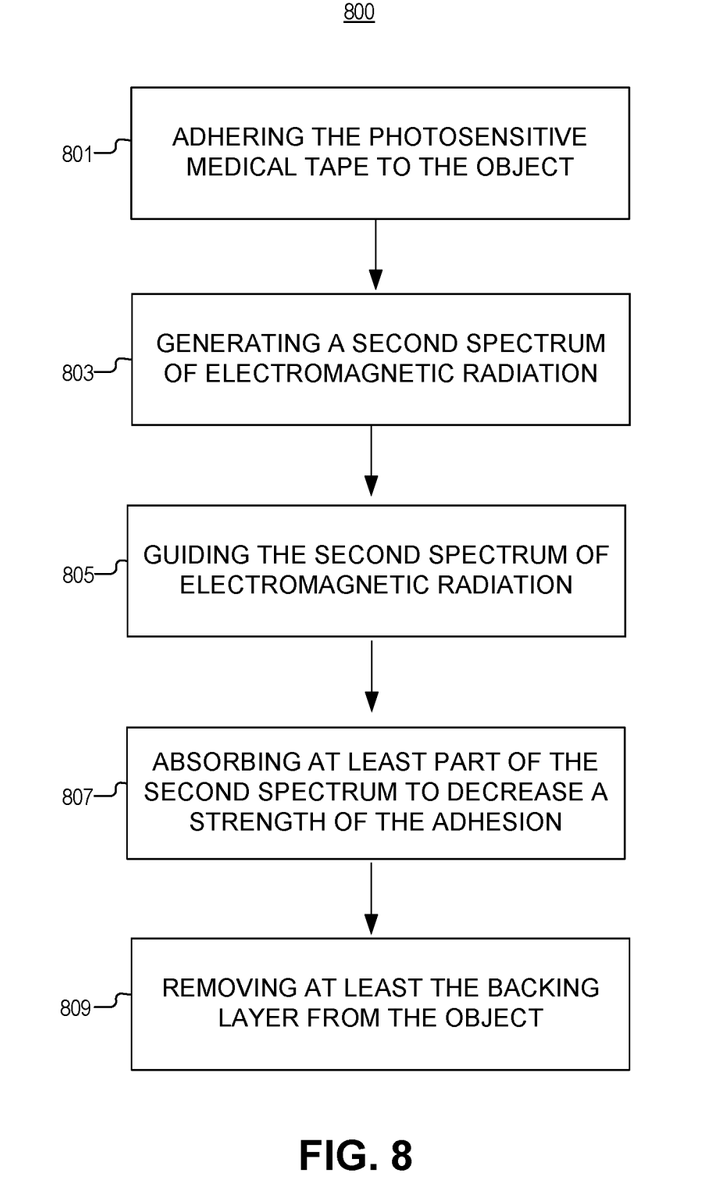
FIG. 8 illustrates an example method for attaching and removing photosensitive medical tape to/from an object, in accordance with the teachings of the present invention.

FIG. 8 illustrates an example method 800 for attaching and removing photosensitive medical tape from an object. Element 801 illustrates adhering the photosensitive medical tape to human skin or a device by bringing a coupling layer disposed on a first side of a backing layer into contact with the human skin. The backing layer is at least partially transparent to a first spectrum of electromagnetic radiation. The coupling layer provides adhesion of the photosensitive medical tape to the object/skin.

Element 803 illustrates generating a second spectrum of electromagnetic radiation with a light source, where the generated second spectrum of electromagnetic radiation is absorbed by the photosensitive medical tape. In one example, the generated second spectrum of electromagnetic radiation has a wavelength of 365 nm.

Element 805 illustrates guiding the generated second spectrum of electromagnetic radiation such that the second spectrum of electromagnetic radiation is incident on the first side of the backing layer while simultaneously pulling the backing layer away from the object/skin.

Element 807 illustrates absorbing at least part of the generated second spectrum of electromagnetic radiation with the coupling layer to decrease a strength of the adhesion provided by the coupling layer.

Element 809 illustrates removing at least the backing layer from the human skin or device.

Method 800 may also include applying a UV or IR blocking barrier film or disinfectant that is swabbed on the arm or the human skin before the photosensitive medical tape is adhered to the human skin. In another example, the light source may be part of arm sleeve 700 described in FIG. 7A. Arm sleeve 700 may be wrapped around the arm and the photosensitive medical tape. A timer may be set on arm sleeve 700 that generates the second spectrum of electromagnetic energy for a predetermined amount of time. After the predetermined set of time expires, arm sleeve 700 may stop generating the second spectrum of electromagnetic radiation and arm sleeve 700 may then be removed from the arm. The arm sleeve may then be cleaned for re-use on another patient.

The above description of illustrated examples of the invention, including what is described in the Abstract, is not intended to be exhaustive or to limit the invention to the precise forms disclosed. While specific examples of the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific examples disclosed in the specification. Rather, the scope of the invention is to be determined entirely by the following claims, which are to be construed in accordance with established doctrines of claim interpretation.

The embodiments of the invention in which an exclusive property or privilege is claimed are defined as follows:

1. A photosensitive medical tape for attachment to human skin, the photosensitive medical tape comprising:
    a backing layer, wherein the backing layer is at least partially transparent to a first spectrum of electromagnetic radiation;
    a coupling layer disposed on a first side of the backing layer to provide adhesion of the photosensitive medical tape to the human skin, wherein a strength of the adhesion provided by the coupling layer decreases in response to an absorption of a second spectrum of electromagnetic radiation by the photosensitive medical tape, and wherein the photosensitive medical tape is flexible; and
    a plurality of dye molecules to provide the absorption of the second spectrum of electromagnetic radiation and cause an increase of temperature in at least part of the photosensitive medical tape.

2. The photosensitive medical tape of claim 1, wherein the first spectrum of electromagnetic radiation includes a visible spectrum of electromagnetic radiation and the second spectrum of electromagnetic radiation.

3. The photosensitive medical tape of claim 2, wherein the coupling layer is at least partially transparent to the visible spectrum of electromagnetic radiation.

4. The photosensitive medical tape of claim 1, wherein the plurality of dye molecules is dispersed in at least one of the backing layer, the coupling layer, or a sacrificial thin film, wherein the sacrificial thin film is disposed between the coupling layer and the backing layer.

5. The photosensitive medical tape of claim 1, wherein a first portion of the coupling layer proximate to the backing layer has a glass transition temperature greater than the glass transition temperature of a second portion of the coupling layer.

6. The photosensitive medical tape of claim 1, wherein the coupling layer includes a plurality of photoactive molecules, wherein upon the absorption of the second spectrum of electromagnetic radiation the plurality of photoactive molecules initiate a chemical reaction within the coupling layer to decrease the strength of the adhesion provided by the coupling layer.

7. The photosensitive medical tape of claim 6, wherein the plurality of photoactive molecules are disposed in a first portion of the coupling layer in contact with the backing layer, and wherein the first portion of the coupling layer is a thin film.

8. The photosensitive medical tape of claim 1, wherein an inner backing layer is disposed between a first portion and a second portion of the coupling layer, and wherein the second portion of the coupling layer adheres to the human skin.

9. A system for attachment to human skin, the system comprising:
    a light source to generate a second spectrum of electromagnetic radiation;
    a photosensitive medical tape to receive the second spectrum of electromagnetic radiation from the light source, wherein the photosensitive medical tape is flexible and includes:
        a backing layer that is at least partially transparent to a first spectrum of electromagnetic radiation;
        a coupling layer disposed on a first side of the backing layer to provide adhesion of the photosensitive medical tape to the human skin, and wherein a strength of the adhesion provided by the coupling layer decreases in response to an absorption of the second spectrum of electromagnetic radiation by the photosensitive medical tape; and
        a plurality of energy absorbing particles to provide the absorption of the second spectrum of electromagnetic radiation and cause an increase in temperature of at least part of the photosensitive medical tape.

10. The system of claim 9, wherein the first spectrum of electromagnetic radiation includes a visible spectrum of electromagnetic radiation and the second spectrum of electromagnetic radiation.

11. The system of claim 9, wherein the plurality of energy absorbing particles is dispersed in at least one of the backing layer, the coupling layer, or a sacrificial thin film, wherein the sacrificial thin film is disposed between the coupling layer and the backing layer.

12. The system of claim 9, wherein the plurality of energy absorbing particles is dispersed within the coupling layer, and wherein a concentration of the plurality of energy absorbing particles is uniform throughout the coupling layer.

13. The system of claim 9, wherein the plurality of energy absorbing particles is dispersed within the coupling layer, and wherein a concentration of the plurality of energy absorbing particles is non-linear throughout a thickness of the coupling layer.

14. The system of claim 13, wherein the concentration of the plurality of energy absorbing particles increases as a step function in a direction away from the backing layer.

15. The system of claim 9, wherein the coupling layer includes a plurality of photoactive molecules, wherein upon the absorption of the second spectrum of electromagnetic radiation the plurality of photoactive molecules initiate a chemical reaction within the coupling layer to decrease the strength of the adhesion provided by the coupling layer.

16. The system of claim 9, further comprising:
a wand coupled to the light source, the wand to focus the generated second spectrum of electromagnetic radiation at a tip of the wand.

17. A method for attaching and removing a photosensitive medical tape to an object, the method comprising:
adhering the photosensitive medical tape to the object by bringing a coupling layer disposed on a first side of a backing layer into contact with the object, the coupling layer to provide adhesion of the photosensitive medical tape to the object, and wherein the backing layer is at least partially transparent to a first spectrum of electromagnetic radiation;
generating a second spectrum of electromagnetic radiation with a light source, wherein the generated second spectrum of electromagnetic radiation is absorbed by the photosensitive medical tape; and
absorbing at least part of the generated second spectrum of electromagnetic radiation with a plurality of dye molecules to cause an increase of temperature of at least part of the photosensitive medical tape, and wherein a strength of adhesion provided by the coupling layer decreases in response to the absorption of the generated second spectrum of electromagnetic radiation by the photosensitive medical tape; and
removing at least the backing layer from the object.

18. The method of claim 17, further comprising:
guiding the generated second spectrum of electromagnetic radiation such that the second spectrum of electromagnetic radiation is incident on the first side of the backing layer while simultaneously pulling the backing layer away from the object.

* * * * *